(12) United States Patent
Jaeger (10) Patent No.: US 11,806,467 B2
(45) Date of Patent: Nov. 7, 2023

(54) FILTER ASSEMBLY, SURGICAL SUCTION SYSTEM, AND METHOD OF MAKING A BONE-REPAIR ELEMENT WITH AUTOLOGOUS TISSUE INCLUSIONS

(71) Applicant: Marcus Jaeger, Essen (DE)

(72) Inventor: Marcus Jaeger, Essen (DE)

( * ) Notice: Subject to any disclaimer, the term of this patent is extended or adjusted under 35 U.S.C. 154(b) by 999 days.

(21) Appl. No.: 16/433,497

(22) Filed: Jun. 6, 2019

(65) Prior Publication Data
US 2019/0381224 A1    Dec. 19, 2019

(30) Foreign Application Priority Data

Jun. 14, 2018  (DE) .......................... 102018114304.4
Apr. 2, 2019   (EP) ..................................... 19166834

(51) Int. Cl.
| | | |
|---|---|---|
| *A61M 1/00* | (2006.01) | |
| *A61L 27/12* | (2006.01) | |
| *A61L 27/36* | (2006.01) | |
| *A61L 27/38* | (2006.01) | |
| *A61B 17/88* | (2006.01) | |
| *A61M 1/38* | (2006.01) | |

(52) U.S. Cl.
CPC ............... *A61M 1/79* (2021.05); *A61L 27/12* (2013.01); *A61B 17/8827* (2013.01); *A61B 2217/005* (2013.01); *A61L 27/3608* (2013.01); *A61L 27/3886* (2013.01); *A61M 1/38* (2013.01)

(58) Field of Classification Search
CPC ....... A61B 17/8827; A61M 1/00; A61M 1/79; A61M 1/76
See application file for complete search history.

(56) References Cited

U.S. PATENT DOCUMENTS

| | | | | |
|---|---|---|---|---|
| 4,468,217 | A * | 8/1984 | Kuzmick ................ | A61M 1/76 433/92 |
| 4,886,492 | A * | 12/1989 | Brooke .................... | A61M 1/79 604/902 |
| 6,406,454 | B1 * | 6/2002 | Hajianpour ............. | A61M 1/76 604/48 |
| 2008/0071192 | A1 * | 3/2008 | Hynes ..................... | A61M 1/74 600/562 |
| 2014/0331863 | A1 * | 11/2014 | Xiang ..................... | A61M 1/63 96/134 |
| 2014/0363403 | A1 * | 12/2014 | Segina .................... | A61P 41/00 604/319 |
| 2018/0353206 | A1 * | 12/2018 | Assell ................ | A61B 17/3472 |
| 2019/0209765 | A1 * | 7/2019 | Shimada ................ | B01D 39/16 |

* cited by examiner

*Primary Examiner* — Adam Marcetich
*Assistant Examiner* — Meagan Ngo
(74) *Attorney, Agent, or Firm* — Andrew Wilford (57) ABSTRACT

A filter assembly for a surgical suction system. The filter assembly has a containment defining a filter chamber an intake fitting on an upstream end of the chamber, an output fitting on an opposite downstream end of the chamber, and a filter element in the filter chamber and made at least partially of a bioresorbable bone substitute so that autologous tissue components carried in a fluid flowing from the fitting through the filter element in the filter chamber are trapped by the filter element.

10 Claims, 3 Drawing Sheets

Fig.1

FILTER ASSEMBLY, SURGICAL SUCTION SYSTEM, AND METHOD OF MAKING A BONE-REPAIR ELEMENT WITH AUTOLOGOUS TISSUE INCLUSIONS

FIELD OF THE INVENTION

The present invention relates to a filter assembly. More particularly this invention concerns a surgical suction system and method of making a bone-repair element with autologous tissue inclusions.

BACKGROUND OF THE INVENTION

A typical filter assembly for a surgical suction system has a containment forming a filter chamber and with an intake fitting at one end and an output fitting at an opposite end. A filter element is held in the chamber and flow from the intake fitting is routed in the chamber through the filter element and then out the output fitting.

Various versions of filter assemblies of the above-described type are known from practice. Such filter assemblies are used in surgical suction systems used for example in orthopedic operations, particularly on the human body. The surgical suction systems are used to suction off blood and released loose tissue components, such as bone particles. Such suction systems generally have a pump and are usually followed by other devices or follow-up systems such as autotransfusion systems. The functionality of such follow-up systems would be adversely affected by aspirated tissue components such as for example bone fragments. For this reason, filter assemblies are often used in surgical suction systems in order to retain such components.

However, the filter assemblies or filter elements that are known from practice have a number of disadvantages. As a rule, they quickly fill with the aspirated tissue components, thus becoming clogged and having to be exchanged. However, in most disposable filter assemblies the filter element is inaccessible and securely fixed or placed in a housing. When a filter element becomes loaded and/or clogged, both the filter element and the housing are discarded. This is not very economical. Furthermore, the tissue components trapped or retained using the known filter assemblies or filter elements are discarded unused with the filter assembly or with the filter element. This is disadvantageous both economically and medically. The tissue components trapped or retained by the filter elements have osteoregenerative potential. They are thus suitable for bone regeneration and for the treatment of bone defects. This osteoregenerative potential is not exploited in the measures that are known from practice. In many of the known systems, it is not possible to separate the tissue components from the filter assembly or from the filter element, or such a measure would be associated with considerable effort and expense. A need for improvement exists in this regard.

OBJECTS OF THE INVENTION

It is therefore an object of the present invention to provide an improved filter assembly and surgical suction system.

Another object is the provision of such an improved filter assembly, surgical suction system, and method of making a bone-repair element that overcomes the above-given disadvantages, in particular with which the disadvantages described above can be avoided in an effective and simple manner, that operates in a functionally reliable manner over a sufficiently long period of time, adequately satisfies all the requirements from an economic perspective, and is also suitable for exploiting the osteoregenerative potential of the extracted tissue components and/or rendering them useful.

Another object is to provide a method of making a bone substitute that includes autologous tissue components, a filter element, and a use of such a bone substitute or filter element in a method of the treatment of bone defects in the human body.

SUMMARY OF THE INVENTION

A filter assembly for a surgical suction system. The filter assembly has according to the invention a containment defining a filter chamber an intake fitting on an upstream end of the chamber, an output fitting on an opposite downstream end of the chamber, and a filter element in the filter chamber and made at least partially of a bioresorbable bone substitute so that autologous tissue components carried in a fluid flowing from the fitting through the filter element in the filter chamber are trapped by the filter element.

In other words the invention is a filter assembly for a surgical suction system and comprises an intake fitting, an output fitting, and a filter chamber between the intake fitting and the output fitting. At least one filter element is in the filter chamber and is made at least in part on the basis of at least one bone substitute, preferably a bioresorbable bone substitute so that autologous tissue components that are carried in a fluid flowing through the filter assembly can be separated off by the filter element.

According to a second embodiment, the filter element is made at least in part on the basis of at least one carrier material based on at least one plastic, and the bone substitute within the filter element is inside the filter element. In this second embodiment of the invention, the carrier material or the plastic is advantageously a polymeric plastic, preferably a polymeric acrylate or a polymeric methacrylate. Especially preferably, is the carrier material for the filter element is polymethyl methacrylate (PMMA). In the case of a hollow filter element, it lies within the scope of the invention for its walls or shell to consist or substantially consist of the carrier material, more particularly of the aforementioned plastic. In this second embodiment according to the invention, the bone substitute that is in the filter element, particularly bioresorbable bone substitute, is preferably in the form of particles, more particularly small particles, and particularly in the form of granulate inside the filter element. As will be explained below, if the filter element has holes, it also lies within the scope of the invention for the diameter of the particles or granulate particles to be greater than the diameter of the holes. The particles are thus prevented from getting out of the filter element and being effectively wetted with the autologous tissue components during a suction procedure. In principle, the particles of the bone substitute can be chips, small beads, cubes, cuboids, or the like.

In the first embodiment in which the filter element is made at least in part on the basis of at least one bone substitute, it lies within the scope of the invention for this filter element to be filled with a bone substitute, particularly in the form of particles, more particularly small particles.

In the context of the invention, a "surgical suction system" refers in particular to a suction system that is used during an operation, preferably on the human body, during which a fluid consisting of fat, bone marrow, blood, and other tissue components is aspirated. This fluid also contains solid tissue components such as cartilage fragments and bone fragments, as well as highly viscous components such as coagula, fats, and the like. Such a surgical suction system can have a suction device in the form of a pump as well as a suction device with which the fluid is aspirated at the surgical site, for example via a suction hose or a suction tube or the like. In addition, at least one collecting vessel for the fluid can be provided. It lies within the scope of the invention for the filter assembly according to the invention with which the solid and/or highly viscous tissue components can be separated from the aspirated fluid to be between the suction device and the collecting vessel for the fluid.

In the context of the invention, the terms "fluid" and "fluid flowing through the filter assembly" thus refer particularly to the mainly liquid fluid that is aspirated using the surgical suction system in the course of an operation.

In the context of the invention, "autologous tissue components" are particularly endogenous tissue constituents that are part of the fluid that is aspirated by the surgical suction system or that are entrained in this fluid.

In the context of the invention, the term "bone substitute" refers in particular to a substance that can be used to fill in bone defects, particularly on or in human bone, if the body's own bone material is not available or not in sufficient quantity. In this context, "bioresorbable bone substitute" refers particularly to a bone substitute that itself degrades or dissolves in the body, preferably in the human body, after a certain time or is degraded by cells and/or tissue fluids. Such bioresorbable bone substitutes are therefore also referred to as biodegradable bone substitutes or self-dissolving bone substitutes.

In the context of the invention, "filter element" refers particularly to an element through which a fluid can pass while components such as solids or highly viscous substances that are carried along are trapped or retained at least in part by the filter element.

One especially preferred embodiment of the filter assembly according to the invention is characterized in that the filter element is hollow. The hollow filter element forms an inner compartment, and the filter chamber of the filter assembly very especially preferably encloses the filter element. Advantageously, the filter chamber encloses the filter element such that an outer compartment is between the outer surface of the filter element and the inner surface of containment forming the filter chamber. In this context, "flow space" refers in particular to a space in which the fluid can flow or through which the fluid can flow.

According to the invention, the filter assembly has at least one intake fitting, at least one output fitting, and at least one filter chamber, and the at least one filter element is in the filter chamber. It is recommended that the inner compartment of the filter element be in fluid communication with the intake fitting. The intake fitting of the filter assembly serves to allow or conduct the fluid that is aspirated with the surgical suction system into the filter chamber. According to a preferred embodiment, when the inner compartment is in fluid communication with the intake fitting, the fluid preferably passes through the intake fitting into the inner compartment of the filter element.

It has proven advantageous if the outer compartment is in fluid communication with the output fitting. The output fitting according to the invention serves to conduct or allow the fluid out of the filter chamber. Advantageously, the fluid flowing through the filter assembly must pass through the filter element in order to travel from the inner compartment to the outer compartment. From the outer compartment, the filtered fluid, or filtrate, then preferably passes out of the filter chamber and/or out of the filter assembly via the output fitting.

It lies within the scope of the invention for the intake fitting to be in fluid communication only with the inner compartment of the filter element on the filter chamber side and/or for the output fitting to be in fluid communication only with the outer compartment on the filter chamber side. This embodiment is based on the discovery that the fluid then passes through the intake fitting into the filter chamber and directly into the inner compartment of the filter element. Preferably, the fluid must then pass from inner compartment inside the hollow filter element to the outer compartment outside through the hollow filter element and thus enter the outer compartment. If the output fitting is advantageously only in fluid communication with the outer flow chamber on the filter chamber side, the filtered fluid is then subsequently guided out of the filter chamber and/or out of the filter assembly through the output fitting. Incidentally, in the context of the invention, the expression "exclusive fluid communication" refers to the direct fluid connection that does not affect or exclude passage through the filter element. In principle, it also lies within the scope of the invention for the inner compartment to be in fluid communication with the output fitting or for the output fitting to be in fluid communication only with the inner compartment on the filter chamber side and/or for the outer compartment to be in fluid communication with the intake fitting or for the intake fitting to be in fluid communication only with the outer compartment on the filter chamber side. In such an embodiment, the filter assembly is then provided so that the aspirated fluid first passes through the intake fitting into the outer compartment, then passes through the hollow filter element from the outside to the inside, and is then allowed or conducted from the inner compartment via the output fitting and out of the filter assembly.

According to an especially preferred embodiment of the invention, the filter element is tubular. Such a tubular filter element preferably has an opening at each of its end faces, and the tubular filter element advantageously has a six-sided or hexagonal cross section. According to an alternative embodiment, the cross section of the filter element is circular. In principle, other cross sectional geometries of the tubular filter element, such as square, rectangular, triangular, star-shaped, oval-shaped, and the like, are within the scope of the invention.

If the filter element according to the preferred embodiment is tubular, it is recommended that at least one end of the filter element be closed in the assembled state of the filter element. Especially preferably, the end facing toward and/or associated with the output fitting or the opening of the filter element facing toward and/or associated with the output fitting is closed in the assembled state of the filter element. This embodiment is based on the discovery that the fluid can then preferably pass via the intake fitting and the open end of the tubular filter element into the inner compartment and then cannot escape from the filter element at the opposite end of the filter element, but rather must radially of the element axis pass through the filter element in particular in order to get into the outer compartment. In this context, "assembled state of the filter element" refers particularly to the state of the filter element in which it is located in the filter chamber and in which the filter assembly is ready for use.

The closure of one end of the tubular filter element can be achieved by a closure element on the filter assembly, for example a closure plate or the like. Such a closure element or such a closure plate can be especially preferably provided on the output fitting or, alternatively, on or in the filter chamber, recommendably on the side of the filter chamber facing toward and/or associated with the output fitting. The closure element is advantageously a closure plate. The closure element or the closure plate then advantageously has a centering stub onto which the filter element can be plugged or pushed or that can be plugged or pushed into the filter element, so that the centering stub extends into the filter element in the assembled state of the filter element. It is recommended that a sleeve or ring also be provided with a tubular centering stub on the intake fitting, it being preferably possible for the filter element to be plugged or pushed onto the centering stub so that, in the assembled state of the filter element, the centering stub extends into the filter element. The filter element is then very especially preferably held in the filter chamber by and/or between solid the centering stub of the closure element and/or the closure plate and the tubular centering stub of the sleeve element. In principle, it also lies within the scope of the invention for the closure element or the closure plate to be on the filter element itself or to be part of the filter element.

One embodiment that has very special significance in the context of the invention is characterized in that the outer layer is tubular. Very especially preferably, both the filter chamber and the filter element are tubular and, advantageously, the tubular filter chamber encloses the tubular filter element. Advantageously, the filter chamber has a circular cross-sectional surface. In principle, other cross-sectional surface geometries of the filter chamber, such as six-sided or hexagonal, square, rectangular, and the like, also lie within the scope of the invention.

It also lies within the scope of the invention for the filter element and the filter chamber to be coaxial with one another. Advantageously, the filter element extends longitudinally over a majority of the length of the filter chamber, preferably over at least 70% of the length of the filter chamber, especially preferably over at least 80% of the length of the filter chamber, and very especially preferably over at least 90% of the length of the filter chamber, for example over at least 95% of the length of the filter chamber. According to an especially preferred embodiment, the filter element extends longitudinally over the entire length of the filter chamber or substantially over the entire length of the filter chamber.

One highly recommended embodiment of the invention is characterized in that the intake fitting and/or the output fitting has at least one connection element, preferably a connector, on the side facing away from the filter chamber. By such a connection element, the filter assembly according to the invention can be connected to other devices of the surgical suction system. In particular, the connection elements are suitable for enabling hoses or tubes or the like to be connected to the filter assembly. For this purpose, the connecting element can be embodied, for example, as a conically tapering connector with a fluid passage, for example in the form of an inner tube, that tapers conically in the direction of the side facing away from the filter chamber. In principle, however, other connection elements that are on the side of the intake fitting and/or of the output fitting facing away from the filter chamber also lie within the scope of the invention. According to one embodiment of the invention, the intake fitting has a connection element into which a suction device, for example a suction tube or a suction hose, can be inserted or plugged, and the fluid is suctioned or aspirated by the suction device. According to a preferred embodiment of the invention, if a sleeve element is provided with a centering stub at the intake fitting, it lies within the scope of the invention if a fluid passage of the intake fitting, for example in the form of an inner tube, engages through the sleeve element and if a suction device such as a suction tube or suction hose can be inserted and/or plugged into the inner tube of the intake fitting, and if the suction device then preferably engages through the inner tube and/or the sleeve element and the centering stub. In principle, it also lies within the scope of the invention for the intake fitting of the filter assembly itself to be used directly for suction or aspiration. Preferably, the connection element of the output fitting serves to connect the output fitting to a hose via which the filtered fluid is then conducted further, for example to a collecting vessel or the like.

According to an advantageous embodiment of the invention, at least one connecting element, preferably a screwthread, is provided on the intake fitting and/or on the output fitting on the filter chamber side. The thread is especially preferably an internal thread. It is recommended that the connecting element on the intake fitting and/or on the output fitting on the filter chamber side interacts with a complementary connecting element on the filter chamber, preferably with a compled23ementary thread. The complementary thread is especially preferably a complementary external thread. It has proven advantageous that the intake fitting and/or the output fitting is removable, preferably unscrewable, from the filter chamber. In principle, it also lies within the scope of the invention for an external thread to be provided on the intake fitting and/or on the output fitting that interacts with a complementary internal thread on the filter chamber. It also lies within the scope of the invention for the connecting element and the complementary connecting element to be plug connections. By virtue of the reversible removability of the intake fitting and/or of the output fitting from the filter chamber, the filter assembly can be opened in a simple and functionally reliable manner and that the filter element can then be removed from the filter assembly wholly manually without tools. The filter element can thus be removed and continue to be used without any difficulty. In addition, this embodiment is based on the discovery that a new, unused filter element can be easily introduced into the filter assembly, thus enabling the filter chamber and/or the intake fitting and/or the output fitting to be reused. Moreover, the closure element already mentioned above, particularly a closure plate, can also be on an intake fitting and/or output fitting that can be removed from the filter chamber and be used to seal a tubular filter element at an end face of the filter element. In principle, both the intake fitting and the output fitting can be provided with at least one connecting element on the filter chamber side, and then the filter chamber is provided with complementary connecting elements on its side associated with the intake fitting and on its side associated with the output fitting. According to an alternative and especially preferred embodiment, either the intake fitting or the output fitting is provided with a connecting element and is removable from the filter chamber. It then lies within the scope of the invention for the respective other portion to be integrally formed with the filter chamber and to not be removable from the filter chamber, as it were.

According to an especially recommended embodiment of the invention, a wall thickness of the filter element is between 0.5 mm and 4.0 mm, preferably between 0.7 mm and 3.0 mm, especially preferably between 1.0 mm and 2.5 mm, and very especially preferably between 1.2 mm and 2.0 mm. In the context of the invention, the "wall thickness" of the filter element refers particularly to the wall thickness of the filter element through which the fluid must pass in order to pass through the filter element. In this regard, the wall thickness of the filter element refers particularly to the passage thickness of the filter element. In the case of a filter element that is a hollow body, for example the wall thickness s refers the wall thickness of the tubular filter element. If the filter element according to the first embodiment of the invention is made at least in part on the basis of at least one bone substitute, the filter element can also be a simple filter disk or the like, in which case the wall thickness of the filter element refers particularly to the thickness or passage thickness of such a disk-shaped filter element.

One very especially preferred embodiment of the invention is characterized in that the filter element has a multitude of holes. Such holes are provided in particular as fluid passage holes in the filter element. Especially preferably, the fluid passes only or essentially only through the holes and travels past the filter element and/or passes through the filter element in this way. The selection of the size and/or diameter of the holes, can then determine which constituents of the fluid are not able to pass through the holes due to their size and are trapped or retained by the filter element, as it were. It lies within the scope of the invention for the holes to have a diameter in the range from 0.1 mm to 8.0 mm, preferably between 0.2 mm and 6.0 mm, especially preferably between 0.5 mm and 4.0 mm, and very especially preferably between 1.0 mm and 3.0 mm. In this context, "diameter" refers particularly to the largest diameter of a hole. The holes are preferably provided as round holes. In the case of a tubular filter element according to a preferred embodiment, the holes are especially preferably in the walls of the tubular filter element and very especially preferably round holes. In principle, however, other shapes of holes also lie within the scope of the invention, for example holes with an angular shape, such as square or rectangular holes.

It is recommended that the surface ratio of the holes relative to the surface area of the filter element be between 0.5% and 25%, preferably between 2% and 20%, especially preferably between 3% and 15%, and very especially preferably between 4% and 12%. In relation to the surface area of the filter element, "surface ratio of the holes" means the proportion of the summed opening area of the holes relative to the entire surface area of the filter element without such openings. Preferably, the holes are arrayed uniformly or substantially uniformly in the longitudinal direction of the filter element along the filter element, more particularly along the surface of the filter element. It is recommended that the holes be arrayed in the longitudinal direction of the filter element at a constant spacing or substantially at a constant spacing from one another.

According to the first embodiment of the invention, the filter element is made at least in part on the basis of at least one bone substitute. Preferably, the filter element is made completely of the at least one bone substitute. According to a highly recommended embodiment of the invention, the filter element consists of the at least one bone substitute or the filter element consists substantially of the at least one bone substitute. This embodiment is based on the discovery that the filter element can then consist completely or substantially completely of at least one bone substitute, particularly of at least one bioresorbable bone substitute, and then the filter element, which is provided with autologous tissue components after filtration, is directly suitable for treating bone defects in the human body, since the filter element consists of no ingredients other than the at least one bioresorbable bone substitute.

One embodiment that has very special significance in the context of the invention is characterized in that the at least one bone substitute is a bioresorbable bone substitute. Preferably, the bone substitute is a calcium salt of an acid selected from the group: "phosphoric acid, sulfuric acid, carbonic acid." The bone substitute is especially preferably a calcium phosphate and very especially preferably β-tricalcium phosphate. Furthermore, hydroxyapatite can also be used as a bone substitute. According to one design variant of the invention, the bone substitute is a polylactide or a bioglass.

It lies within the scope of the invention for the filter chamber and/or the intake fitting and/or the output fitting to consist of or substantially consist of at least one polymeric plastic, preferably polymethyl methacrylate (PMMA). It also lies within the scope of the invention for the filter chamber and/or the intake fitting and/or output fitting of at least one polymeric plastic to be selected from the group of polypropylene, polyethylene, polyester, polystyrene, polymethyl methacrylate, and polycarbonate. Preferably, the entire assembly of filter chamber, intake fitting, and output fitting is composed of polymethyl methacrylate (PMMA) or substantially composed of polymethyl methacrylate (PMMA).

The invention also relates, according to a first embodiment, to a method of making a bone substitute that is provided with autologous tissue components in the form of a filter element, wherein a fluid containing autologous tissue components is suctioned into a filter assembly for a surgical suction system, particularly a filter assembly of the type described above, via an intake fitting, and the fluid then flows into a filter chamber in which at least one filter element is arranged, where the filter element is made at least in part on the basis of at least one bone substitute, preferably a bioresorbable bone substitute, wherein the fluid passes through the filter element, wherein at least a portion of the autologous tissue components is trapped or retained by the filter element, and wherein the filtered fluid is subsequently removed from the filter assembly through an output fitting.

The invention further relates, according to a second embodiment, to a method of making a bone substitute that is provided with autologous tissue components, and a fluid containing autologous tissue components is suctioned into a filter assembly for a surgical suction system, particularly a filter assembly of the type described above, via an intake fitting, wherein the fluid then flows into a filter chamber in which at least one filter element is arranged, the filter element being made at least in part of at least one carrier material, particularly on the basis of at least one plastic, wherein at least one bone substitute, particularly a bioresorbable bone substitute, is arranged within the filter element, wherein the fluid passes through the filter element, At least a portion of the autologous tissue components is trapped or retained by the bone substitute that is in the filter element, and the filtered fluid is subsequently removed from the filter assembly through an output fitting.

It lies within the scope of the invention for the filter element to be provided with the autologous tissue components and/or for the filter element that is provided with the autologous tissue components and the bone substitute to be subsequently removed from the filter assembly. This can be done, for example, by unscrewing the intake fitting and/or the output fitting, and the filter chamber and the portion to be unscrewed preferably each have a thread for this purpose, as has already been explained above. The output fitting can be preferably unscrewed from the filter chamber in this way. The filter element can then be removed in a simple and functionally reliable manner from the filter chamber and continue to be used. In addition, after the unscrewing and removal of the inlet and/or the output fitting, a new filter element can be introduced into the filter chamber. The filter element that is provided with autologous tissue components and removed in the context of the first embodiment of the filter chamber is preferably suitable as a bone substitute that is provided with autologous tissue components, especially preferably as a bioresorbable bone substitute. Likewise, the filter element that is provided with autologous tissue components and removed in the context of the second embodiment can also be used analogously.

It is recommended that the shape of the filter element that is provided with the autologous tissue components and/or the bone substitute that is provided with autologous tissue components be adapted after removal from the filter assembly to the site of later application or use. In the context of the first embodiment, the filter element can be crushed for this purpose, for example. Alternatively, however, the filter element can also be used in its original form. The autologous tissue components preferably remain on the filter element or on the bone substitute in the course of the adaptation.

It lies within the scope of the invention for the autologous tissue components to be bone fragments and/or bone marrow and/or coagula and/or fat. Incidentally, the autologous tissue components are particularly human autologous tissue components.

To solve the technical problem, the invention also teaches, in the context of the first embodiment, a filter element that is provided with autologous tissue components, with the filter element being produced by a method described above, and with the filter element being made at least in part, preferably entirely on the basis of a calcium phosphate.

The invention further relates to a use of a bone substitute that is provided with autologous tissue components in the form of a filter element and/or in the form of a bone substitute that is provided with autologous tissue components and removed, produced by a method described above, in a method of treating bone defects in the human body. The bone substitute that is provided with autologous tissue components is preferably a bioresorbable synthetic or allogenic bone substitute and, especially preferably, a calcium phosphate, very especially preferably β-tricalcium phosphate and/or hydroxyapatite. When the filter element that is provided with autologous tissue components and/or the bone substitute that is provided with autologous tissue components is removed from the filter chamber, it can be used as a bone substitute in a method of treating bone defects in the human body. The shape of the filter element or the bone substitute can be adapted to the later site of application or use for this purpose. This use is based on the discovery that a bioresorbable bone substitute is degraded after a certain time and that the autologous tissue components have an osteoregenerative potential, meaning that they stimulate the formation of new bone, as it were. As a result, the tissue components, such as bone particles, that have been extracted during the operation are not discarded, but rather are used together with the filter element made from a bioresorbable bone substitute or together with the bioresorbable bone substitute for the treatment of bone defects in the human body. This is extremely advantageous both from an economic and medical perspective. It is recommended that the bone substitute used be β-tricalcium phosphate. Hydroxyapatite can also be used.

The invention is based on the discovery that the filter assembly according to the invention is simple and easy to handle and that, moreover, the functional reliability of the filter assembly or of the filter element is ensured over a sufficiently long period of time. According to a preferred embodiment of the invention, if the intake fitting and/or the output fitting are removable from the filter chamber, the filter assembly is further characterized in that the filter element can be exchanged and the filter chamber and the intake fitting and the output fitting can be reused. An exchanged filter element that is provided with the autologous tissue components can then be used as a bone substitute that is provided with autologous tissue components. If the filter element according to the first embodiment consists or substantially consists of a bioresorbable bone substitute, such a filter element that is provided with autologous tissue components can be used directly as a bone substitute for treating bone defects in the human body. This can occur, for example, in the context of the same operation in which a fluid is also aspirated using the surgical suction device or in which autologous tissue components are separated off with the filter assembly. In this regard, the filter assembly according to the invention is characterized in that its filter element need not be discarded together with the trapped or separated autologous tissue components after the filtration process, but rather the filter element or the bone substitute can be used to treat bone defects. The filter assembly according to the invention is therefore extremely functionally reliable, has a simple construction, allows easy replacement of the filter element, and meets all requirements in economic terms. It should also be noted that the advantages described above can be achieved through measures that involve little effort and expense. What is more, the filter assembly according to the invention or the method according to the invention for making a bone substitute that is provided with autologous tissue components makes it possible to optimally utilize the osteoregenerative potential of tissue components that are aspirated during an operation. By virtue of the measures according to the invention, the autologous tissue components with osteoregenerative potential need not be discarded after the aspiration and/or filtration, nor need they undergo elaborate separation by a filter element. In this regard, the invention is characterized by substantial advantages in comparison to the measures that are known from practice.

BRIEF DESCRIPTION OF THE DRAWING

The above and other objects, features, and advantages will become more readily apparent from the following description, reference being made to the accompanying drawing in which.

SPECIFIC DESCRIPTION OF THE INVENTION

Figure 1:
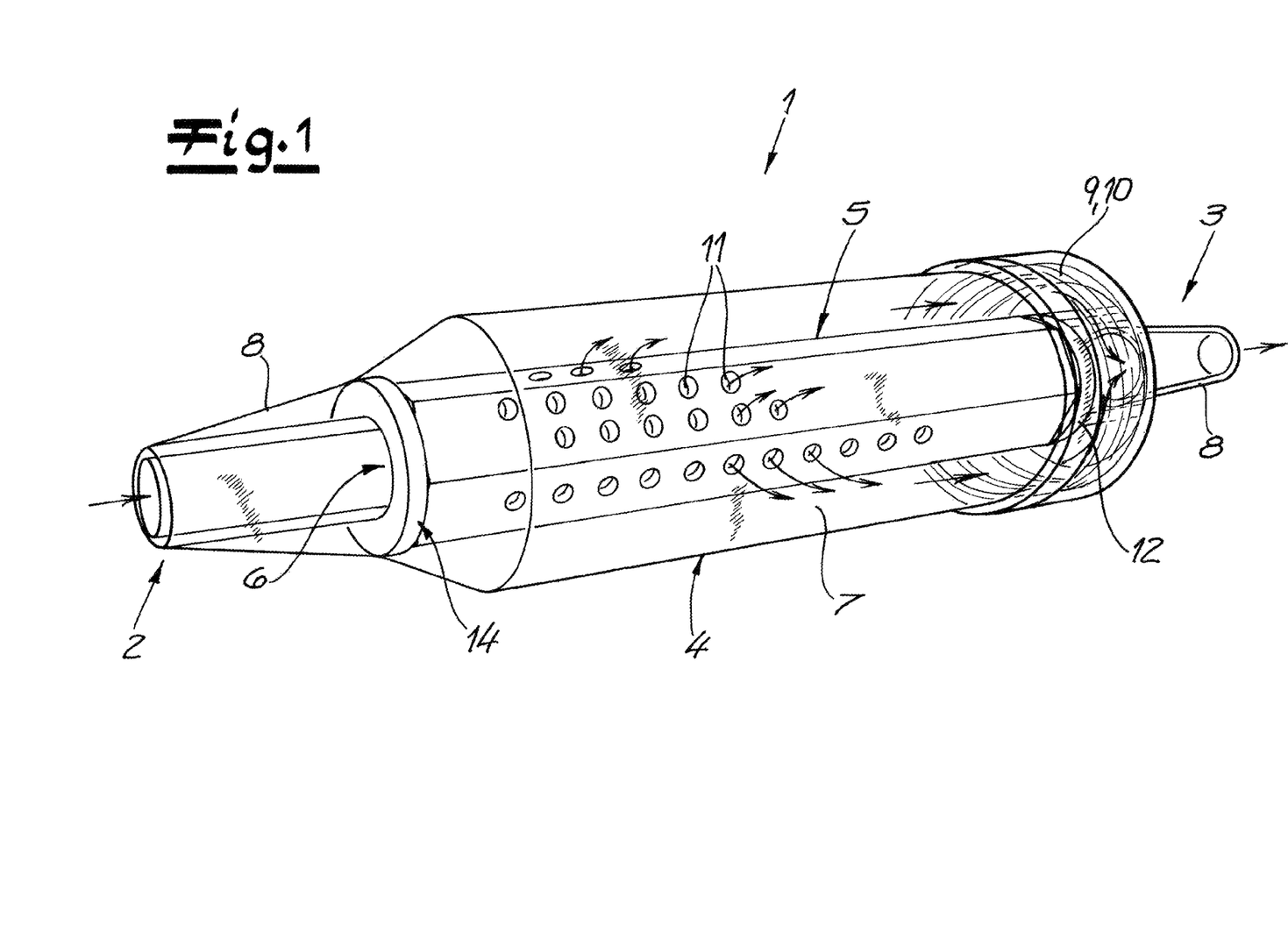
FIG. 1 is a perspective view of a filter assembly according to the invention.
Figure 2:
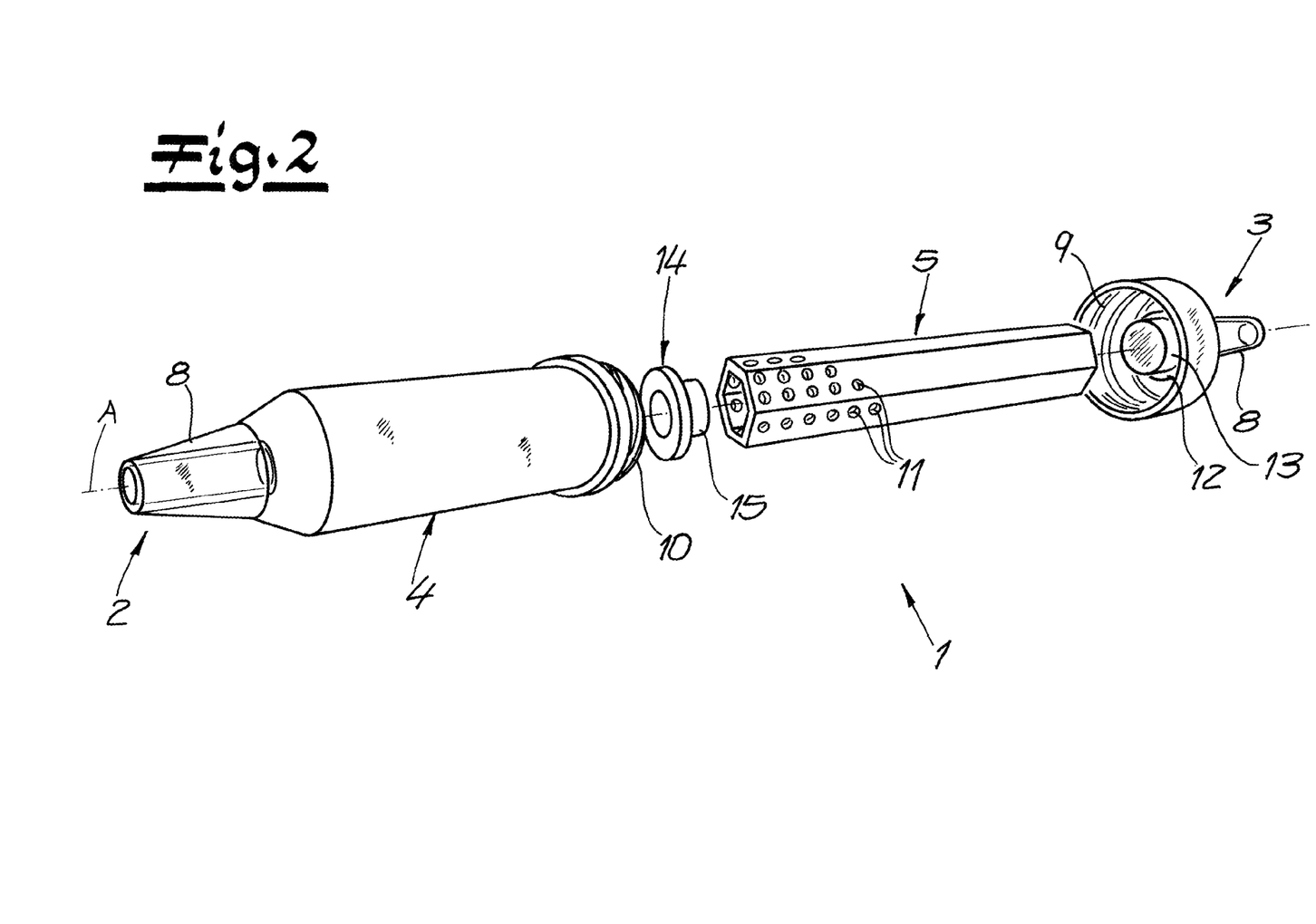
FIG. 2 is an exploded view of the assembly of FIG. 1.

As seen in FIGS. 1 and 2, a filter assembly 1 for a surgical suction system has an intake fitting 2, an output fitting 3, and a containment defining a filter chamber 4 therebetween. A filter element 5 is provided inside the filter chamber 4. According to the first embodiment of the invention, the filter element 5 is made at least in part of at least one bone substitute. In the context of this embodiment and in this embodiment, the filter element 5 is a bone substitute and preferably of a bioresorbable bone substitute. Autologous tissue components that are entrained in a fluid flowing through the filter assembly 1 can be separated from the fluid by the filter element 5.

The filter element is preferably a hollow body and, very especially preferably and in this embodiment according to the figures, the filter element 5 is tubular. Advantageously and in this embodiment, such a tubular filter element 5 is open at each of its ends. The tubular filter element 5 also forms an inner compartment 6 (see FIG. 3 in particular). The filter chamber 4 spacedly surrounds the filter element 5 (FIG. 1) and forms therearound an annular outer compartment 7 between the outer surface of the filter element 5 and the inner surface of the filter chamber 4. This is shown in particular in FIG. 1.

According to a preferred embodiment and here, the inner compartment 6 is in fluid communication with the intake fitting 2, and the outer compartment 7 is in fluid communication with the output fitting 3. Here the fluid flowing through the filter assembly 1 must pass through the filter element 5 in order to travel from the inner compartment 6 to the outer compartment 7. Also, the intake fitting 2 is in fluid communication only with the inner compartment 6 inside the filter element 4, and the output fitting 3 is in fluid communication only with the outer flow chamber 7 surrounding the filter element 4. In this context, "in fluid communication only with" refers to direct fluid connection and does not exclude passage through the filter element between the compartments 6 and 7. The resulting flow path of the fluid is indicated schematically in FIG. 1 by arrows.

Advantageously, the filter element 5 is tubular and here of hexagonal cross section. If the output fitting 3 is in fluid communication only with the outer compartment 7 outside the filter element 4 and the intake fitting 2 is in fluid communication only with the inner flow chamber 6 inside the filter element 4, then an end of the filter element 5, especially preferably the end of the filter element 5 associated with the output fitting 3, is closed in the assembled state of the filter element 5. In this context, "assembled state of the filter element 5" refers particularly to the state of the filter element 5 in which the filter element 5 is in the filter chamber 4 and in which the filter assembly 1 is ready for use. This state is illustrated in FIG. 1.

In order to close one end of the tubular filter element 5 in the assembled state, it is preferred if a closure element, here a closure plate 12, is provided on the output fitting 3 that blocks the open end of the filter element 5 associated with the output fitting 3 in the assembled state of the filter element 5. This closure plate 12 has a centering stub 13 (FIG. 2) of short cylindrical shape centered on a filter center axis A and that can be plugged or pushed into the filter element 5 so that the centering stub 13 extends into the filter element 5 in the assembled state of the filter element 5 (FIG. 1).

Here both the filter element 5 and the filter chamber 4 are tubular, although the latter is cylindrical and centered on the axis A, and the annular filter chamber 4 preferably surrounds the tubular filter element 5. It is recommended that the filter element 5 and the filter chamber 4 be coaxial with one another (FIG. 1). The filter element extends longitudinally over the entire length of the filter chamber or substantially over the entire length of the filter chamber.

The intake fitting 2 and the output fitting 3 each have a connector nipple 8 on the side facing away from the filter chamber 4. Such a connector nipple 8 serves to connect ti additional elements of the surgical suction system. For example, a hose can be connected to the connector 8 of the output fitting 3 in order to further transport the fluid flowing out of the filter assembly 1. The connector 8 of the intake fitting 2 can be used, for example, to receive a suction hose carrying a pickup nozzle.

A washer-like ring 14 that normally closes the upstream end of the chamber 7 is provided with a tubular centering stub 15 on the intake fitting 2, onto which centering stub 15 the filter element 5 can be plugged or pushed so that the centering stub 15 extends into the filter element 5 in the assembled state of the filter element 5 and opens into the compartment 6. The filter element 5 is thus held in the center of the filter chamber 4 in the assembled state by the solid centering stub 13 of the closure plate 12 and the tubular centering stub 15 of the ring 14.

According to a preferred embodiment and here, at least one connecting element is provided on the output fitting 3 on its upstream filter chamber side in the form of an internal thread 9 that interacts with a complementary connecting element in the form of a complementary external thread 10 on the containment forming the chamber 4. The output fitting 3 can thus be removed from, preferably reversibly screwed off the filter chamber 4. The filter element 5 can then be removed in a simple and functionally reliable manner from the filter chamber 4 and be replaced by a new filter element 5 without the use of tools. The internal thread 9 of the output fitting 3 and the complementary external thread 10 of the filter chamber 4 are shown in exploded FIG. 2. Their interaction and their screwed state is illustrated particularly in FIG. 1.

The wall thickness s of the filter element is preferably between 0.7 mm and 3.0 mm, especially preferably between 1.0 mm and 2.5 mm, and very especially preferably between 1.2 mm and 2.0 mm. In this embodiment (see FIG. 3 in particular), the wall thickness s of the filter element 5 may be approximately 1.8 mm. In this context, "thickness" or "wall thickness s of the filter element 5" refers particularly to the thickness or the passage thickness of the filter element 5.

According to a very especially preferred embodiment, the filter element 5 has a multitude of radially thoroughgoing circular holes 11. It is recommended that the fluid passage holes 11 have a diameter a in the range from 0.2 mm and 6.0 mm, preferably between 0.5 mm and 4.0 mm, and especially preferably between 1.0 mm and 3.0 mm. In this embodiment (see FIG. 3 in particular), the wall thickness s of the filter element 11 may be approximately 2.5 mm. In this context, "diameter a" refers particularly to the largest diameter of the fluid passage hole 11, i.e. in the case of a round hole the diameter of the circle.

Figure 3:
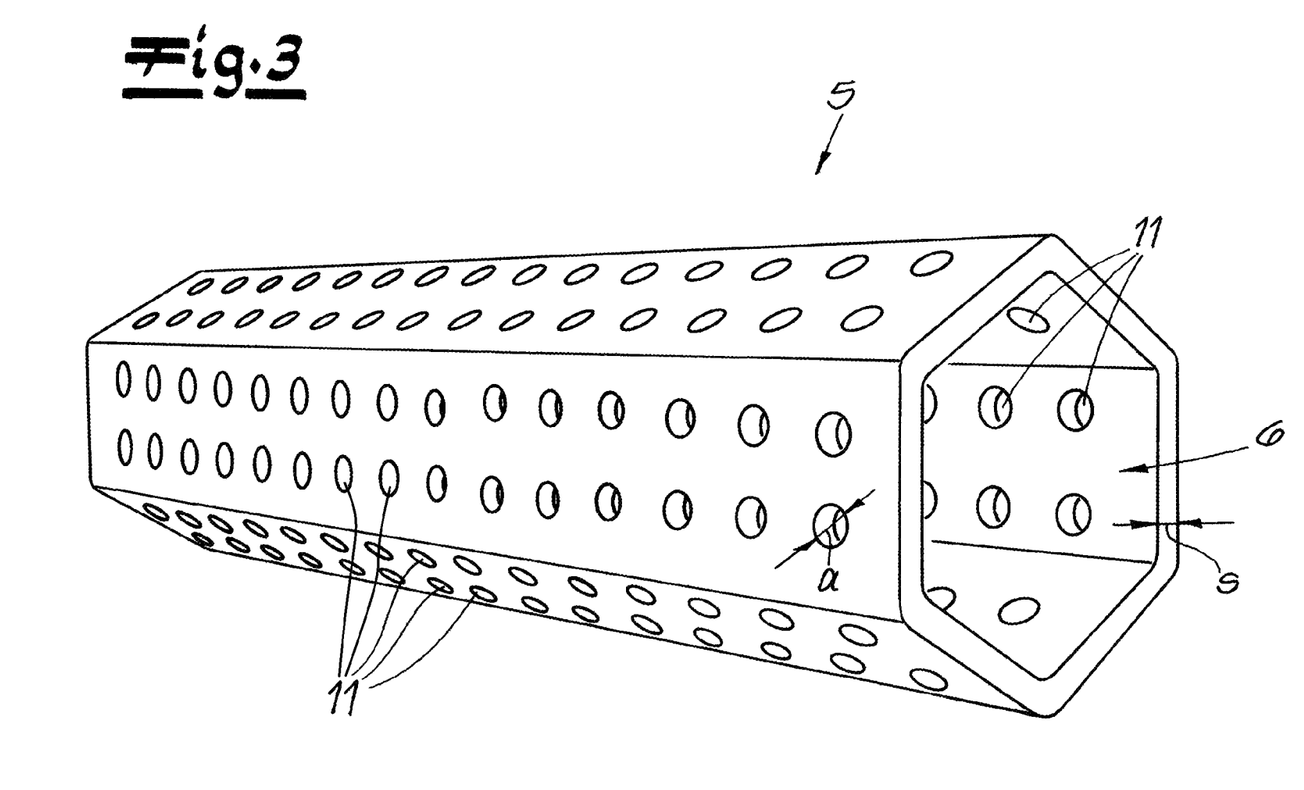
FIG. 3 is a large-scale perspective view of a filter element according to the invention.

It is recommended that the surface ratio of the holes 11 relative to the surface area of the filter element 5 be between 2% and 20%, preferably between 3% and 15%, and very especially preferably between 4% and 12%. In this embodiment according to FIG. 3, the surface ratio of the fluid passage holes 11 to the surface area of the outer surface of the filter element 5 is approximately 9%. In FIG. 3 the holes 11 are arrayed uniformly or substantially uniformly along the filter element 5, more particularly along the surface of the filter element 5. The arrays of holes 11 extend in the longitudinal direction of the filter element 5 at a constant spacing or substantially at a constant spacing from one another.

The fluid extracted by the surgical suction system can flow into the inner compartment 6 through the intake fitting 2 that is in fluid communication only with the inner flow chamber 6 of the tubular filter element 5 on the filter chamber side. The surgical suction system usually has a pump or the like to generate the suction effect. At least one end of the filter element is closed in the assembled state of the filter element 5 that is shown in FIG. 1. In this embodiment (see FIG. 1), the end face of the tubular filter element 5 facing toward the output fitting 3 is closed by the closure plate 12 on the output fitting 3 and closes one end of the filter element 5 in the assembled state of the filter element 5.

The fluid flowing through the filter assembly 1 must pass through the filter element 5 to travel radially from the inner compartment 6 to the outer compartment 7. After passage of the fluid through the holes 11, at least a portion of the autologous tissue components entrained in the fluid remain in the filter element 5 due to their size. The fluid located in the outer compartment 7 can then leave the filter assembly through the output fitting 3 that here is in fluid communication only with the outer compartment 7 on the filter chamber side. Incidentally, the "exclusive fluid communication" is not referring to the fluid connection of the flow spaces due to the holes 11 of the filter element 5.

In the first embodiment of the invention, the filter element 5 consists entirely or substantially of at least one bone substitute. It is recommended that the bone substitute be a bioresorbable bone substitute, preferably a calcium salt of an acid selected from the group of phosphoric acid, sulfuric acid, and carbonic acid. The bone substitute or bioresorbable bone substitute is β-tricalcium phosphate.

It lies within the scope of the invention for the filter chamber 4 and/or the intake fitting 2 and/or the output fitting 3 to consist of at least one polymeric plastic. The assembly of the filter chamber 4 and the intake and output fittings 2 and 3 consists entirely or substantially of PMMA.

I claim:

1. A filter assembly for a surgical suction system, the filter assembly comprising:
   a containment defining a filter chamber:
   an intake fitting on an upstream end of the filter chamber;
   an output fitting on an opposite downstream end of the filter chamber; and
   a filter element in the filter chamber, having openings each of a diameter of 0.2 mm to 6.0 mm, extending over at least 70% of a length of the filter chamber, and consisting of a bioresorbable bone substitute, whereby autologous tissue components carried in a fluid flowing from the intake fitting through the filter element in the filter chamber are trapped by the filter element.

2. The filter assembly defined in claim 1, wherein the filter element is hollow and forms an inner compartment connected to the intake fitting, the containment forming around the filter element an annular outer compartment connected to the output fitting.

3. The filter assembly defined in claim 2 wherein the filter element is constituted such that the fluid can pass radially through from the inner compartment to the outer compartment.

4. The filter assembly defined in claim 2, wherein the intake fitting opens only into the inner compartment and the output fitting opens only into the outer compartment.

5. The filter assembly defined in claim 1, wherein the filter element is tubular and has one open end and one blocked end.

6. The filter assembly defined in claim 5, wherein the filter element and chamber are coaxial.

7. The filter assembly defined in claim 5, wherein a wall thickness of the filter element is between 0.5 mm and 4.0 mm.

8. The filter assembly defined in claim 1, wherein the bone substitute is a calcium salt phosphoric acid, sulfuric acid, or carbonic acid.

9. A filter assembly for a surgical suction system, the filter assembly comprising:
   a containment defining a filter chamber:
   an intake fitting on an upstream end of the filter chamber;
   an output fitting on an opposite downstream end of the filter chamber; and
   a filter element in the filter chamber, having openings each of a diameter of 0.2 mm to 6.0 mm, extending over at least 70% of a length of the filter chamber, and made of an acrylate or methacrylate shell and a lining in the shell of a bioresorbable bone substitute, whereby autologous tissue components carried in a fluid flowing from the intake fitting through the filter element in the filter chamber are trapped by the filter element.

10. The filter assembly defined in claim 9 wherein the bioresorbable bone substitute is constituted as particles lining an inner surface of the shell.

\* \* \* \* \*